(12) United States Patent
Provost et al.

(10) Patent No.: US 12,193,864 B2
(45) Date of Patent: Jan. 14, 2025

(54) METHOD FOR DETERMINING A PROPERTY OF AN OBJECT AND ASSOCIATED DEVICE

(71) Applicants: INSTITUT NATIONAL DE LA SANTE ET DE LA RECHERCHE MEDICALE, Paris (FR); SORBONNE UNIVERSITE, Paris (FR); UNIVERSITÉ PARIS CITÉ, Paris (FR); CENTRE NATIONAL DE LA RECHERCHE SCIENTIFIQUE (CNRS), Paris (FR); ECOLE SUPERIEURE DE PHYSIQUE ET DE CHIMIE INDUSTRIELLES DE LA VILLE DE PARIS, Paris (FR); ASSISTANCE PUBLIQUE—HOPITAUX DE PARIS, Paris (FR)

(72) Inventors: Jean Provost, Paris (FR); Anikitos Garofalakis, Paris (FR); Mathieu Pernot, Paris (FR); Mickaël Tanter, Paris (FR); Bertrand Tavitian, Paris (FR); Thomas Viel, Paris (FR)

(73) Assignees: INSTITUT NATIONAL DE LA SANTE ET DE LA RECHERCHE MEDICALE, Paris (FR); SORBONNE UNIVERSITE, Paris (FR); UNIVERSITÉ PARIS CITÉ, Paris (FR); CENTRE NATIONAL DE LA RECHERCHE SCIENTIFIQUE (CNRS), Paris (FR); ECOLE SUPERIEURE DE PHYSIQUE ET DE CHIMIE INDUSTRIELLES DE LA VILLE DE PARIS, Paris (FR); ASSISTANCE PUBLIQUE—HOPITAUX DE PARIS, Paris (FR)

( * ) Notice: Subject to any disclaimer, the term of this patent is extended or adjusted under 35 U.S.C. 154(b) by 0 days.

(21) Appl. No.: 18/330,502

(22) Filed: Jun. 7, 2023

(65) Prior Publication Data

US 2023/0309944 A1     Oct. 5, 2023

Related U.S. Application Data

(63) Continuation of application No. 15/763,938, filed as application No. PCT/EP2016/073239 on Sep. 29, 2016, now abandoned.

(30) Foreign Application Priority Data

Sep. 29, 2015   (EP) .................................. 15306533

(51) Int. Cl.
*A61B 6/00*     (2024.01)
*A61B 6/03*     (2006.01)
(Continued)

(52) U.S. Cl.
CPC ............ *A61B 6/5247* (2013.01); *A61B 6/032* (2013.01); *A61B 6/037* (2013.01); *A61B 6/4258* (2013.01);
(Continued)

(58) Field of Classification Search
None
See application file for complete search history.

(56) References Cited

U.S. PATENT DOCUMENTS

| | | | | |
|---|---|---|---|---|
| 2006/0237652 A1* | 10/2006 | Kimchy | ............... | G01R 33/481 600/407 |
| 2008/0208044 A1* | 8/2008 | Lecoq | .................. | A61B 8/5238 600/440 |

(Continued)

OTHER PUBLICATIONS

"Tanter et al.," "Ultrafast Imaging in Biomedical Ultrasound," IEEE Transactions on Ultrasonics, Ferroelectrics, and frequency control, vol. 61, No. Jan. 1, 2014.*

*Primary Examiner* — Patricia J Park
(74) *Attorney, Agent, or Firm* — WC&F IP

(57) ABSTRACT

The invention relates to a method for determining at least one property of an object, the method comprising a step of:
(Continued)

a) obtaining first data relative to the object by an ultrasound imaging technique imaging the object at a frame rate superior to 300 Hz, characterized in that the method further comprises a step of: b) obtaining second data relative to the object by imaging the object with at least one of a X-ray and a γ-ray, and c) determining the at least one property of the object based on the first data and the second data.

11 Claims, 1 Drawing Sheet

(51) Int. Cl.
*A61B 6/42* (2024.01)
*A61B 8/00* (2006.01)
*A61B 8/06* (2006.01)
*A61B 8/08* (2006.01)
*A61N 7/00* (2006.01)

(52) U.S. Cl.
CPC .............. *A61B 6/4417* (2013.01); *A61B 8/06* (2013.01); *A61B 8/4416* (2013.01); *A61B 8/488* (2013.01); *A61B 8/5261* (2013.01); *A61N 7/00* (2013.01)

(56) References Cited

U.S. PATENT DOCUMENTS

| | | | |
|---|---|---|---|
| 2010/0198063 A1* | 8/2010 | Huber | A61B 5/05 250/363.03 |
| 2014/0060197 A1* | 3/2014 | Anderson | G01N 29/265 73/634 |
| 2014/0276032 A1* | 9/2014 | Majewski | A61B 8/4254 600/431 |

* cited by examiner

METHOD FOR DETERMINING A PROPERTY OF AN OBJECT AND ASSOCIATED DEVICE

TECHNICAL FIELD OF THE INVENTION

The present invention concerns a method for determining at least one property of an object. The present invention also relates to an associated device.

BACKGROUND OF THE INVENTION

Conventional Ultrasound Imaging (CUI) is the most widely used imaging modality in the clinic as it is portable, real-time, low-cost, and fully non-invasive.

CUI is used in multiple modes that provide different kinds of contrast sources. The B-mode is the standard anatomical imaging mode and relies on the acoustic impedance of tissue, which, while providing limited specificity, has the notable advantage of allowing for the visualization of rapidly moving structures such as the heart. A distinctive feature of these B-mode ultrasound images is the presence of speckle of which the signature can be tracked from one frame to the other and can be used to quantify blood flow and tissue motion in 'Doppler' modes, as long as high frame rates are achieved.

Unfortunately, a fundamental trade-off exists in CUI: to achieve a higher frame rate and thus a high quality functional imaging, a small field of view has to be defined. Indeed, to acquire a conventional ultrasound image, an ultrasound transducer in contact with the skin of the patient is used to emit an ultrasound pulsed wave and to receive the echoes reflected, for instance, by organs, blood vessels or fat.

In CUI, the emitted sound is focused in the form of a beam, as if looking into a dark room with a flashlight. Many of these beams are emitted sequentially and the returning echoes are recorded and combined to, finally, form an image, beam-by-beam. It is a relatively time-consuming process that leads to imaging rates near the real-time threshold of approximately 30 images per second.

Ultrafast Ultrasound Imaging (UUI) is a novel approach to image formation in ultrasound imaging developed in large part by the Institut Langevin in Paris.

To image faster, UUI is based on a different approach in which the entire field of view is insonified using unfocused ultrasound waves. To pursue with the dark room analogy, a light switch in the dark room is flipped on, resulting in the room being flooded with light, and the echoes detected at tens to hundreds of locations are simultaneously recorded for further processing. Since a two dimension ultrasound image typically consists of a hundred beams and UUI can image an entire plane in a single emission, UUI provides a frame rate that is at least 100 times higher than CUI in two dimensions.

Increasing the frame rate by two orders of magnitude renders such technique at least competitive with magnetic resonance imaging. In some cases, the resolution reached by UUI is better than the resolution provided by magnetic resonance imaging.

However, UUI is a physiological imaging technique and as such is unable to achieve sensitive molecular imaging. It is therefore desired to use an imaging technique which would benefit from the advantages of UUI and to reach the molecular stage.

To reach such goal, research in the ultrasound field is intensive.

For instance, ultrafast Doppler imaging has been developed. The ultrafast Doppler imaging mode provides maps of the microvasculature with a 50-fold increase in sensitivity when compared to CUI Doppler modes and does not require the injection of a contrast agent. Furthermore, it can quantify the hemodynamics within those blood vessels, hence allowing for the imaging of brain activation with unprecedented spatial and temporal resolution.

It is also known another imaging mode named "electromechanical wave imaging mode". The electromechanical wave imaging mode uses the gain in motion detection sensitivity to track the propagation of the minute displacements and strains associated with the electromechanical wave in the heart. It is the only imaging modality capable of tracking the transmural propagation of electrical activation in the human heart in vivo.

Finally, the shear-wave Imaging mode uses the ultrasonic radiation force to generate, and UUI to track a shear wave, of which velocity can then be quantified. The stiffness of tissue can be obtained from the shear-wave velocity and has become a powerful biomarker in cardiology and oncology applications.

3D and 4D UUI have also been developed recently. Ultrafast Doppler Tomography consists in concatenating multiple 2D UUI images obtained using a motorized 1-D linear array probe. Since the resolution of a 1-D array is different in all three directions (axial, lateral, and elevational), the array is not only translated but also rotated to ensure high and uniform lateral and elevational resolutions. This approach allows for the use of high-frequency probes and can provide exquisite 3-D images of vasculature, of, e.g., a growing tumor.

However, Ultrafast Doppler Tomography requires long acquisition times, and is thus limited in applications in which dynamic information would be useful (e.g. to track brain activation).

SUMMARY OF THE INVENTION

The invention aims at providing an imaging technique enabling to access the molecular stage and benefiting from the spatial and temporal resolutions reached in UUI techniques.

To this end, the present specification describes a method for determining at least one property of an object, the method comprising the steps of:
  a) obtaining first data relative to the object by imaging the object according to a first modality, the first modality being an ultrasound imaging technique imaging the object at a frame rate superior to 300 Hz,
  b) obtaining second data relative to the object by imaging the object according to a second imaging modality based on the detection of rays, each detected ray being a X-ray or a y-ray,
  c) determining the at least one property of the object based on the first data and the second data.

The use of a combination of data obtained by ultrafast ultrasound imaging with data obtained by a technique involving X-ray and/or a y-ray enables to achieve molecular imaging at UUI spatial and temporal resolution.

Such molecular imaging results in a method adapted to image biochemistry, function and structure which will enable to develop pre-clinical field of research and new clinical diagnostic protocols.

According to further aspects of the method which are advantageous but not compulsory, the method for obtaining which is described in the present specification might incorporate one or several of the following features, taken in any technically admissible combination:

step b) is carried out by using a computed tomography technique.
step b) is carried out by using a γ-scintigraphy technique.
step a) is carried out at a first plurality of time instants, step b) is carried out at a second plurality of time instants and at least one time instant of the first plurality being equal to one time instant of the second plurality.
step a) comprises applying unfocused ultrasound waves.
step a) comprises applying multiple ultrasound planes waves simultaneously.
step a) further comprises the sub-steps of:
a1) emitting ultrasound waves towards the object,
a2) collecting the ultrasound waves reflected by the object,
a3) using the collected ultrasound waves to obtain images, and
a4) analyzing the images to obtain the first data.
the ultrasound imaging technique is chosen in the group consisting of functional ultrasound imaging, electromechanical wave imaging, shear-wave imaging, three-dimensional ultrafast ultrasound imaging and four-dimensional ultrafast ultrasound imaging.
the first data are the movement of the object.
the first data are the movement of the object and step c) comprises correcting the images obtained at step b) based on the first data, to obtain reconstructed images.
the method further comprises the steps of:
d) evaluating the attenuation of a y-ray by the presence of ultrasound waves, and
e) compensating the evaluated attenuation by using a computed tomography technique.
step b) is carried out by using a positron emission tomography technique.
at step b), γ-rays are detected, the detection of γ-ray being in coincidence.
step b) and step e) are carried out simultaneously.
the object is a biological object studied in a field, the field being oncology, cardiology or neurology.
the first data are the movement of the object and step c) comprising correcting the images obtained at step b) based on the first data, to obtain reconstructed images.
step a) is carried out with an ultrasound probe which is hold by a support.
the support is displaceable.
the support is a rod maintained by a positioner.
step a) is carried out with an ultrasound probe and step a) comprising displacing the ultrasound probe in function of the movement of the object from one image to another image.
step a) further comprises displacing the ultrasound probe in function of hemodynamics data.
at step a), at least one of the following properties is fulfilled:
step a) comprises applying unfocused ultrasound waves
step a) comprises applying multiple ultrasound plane waves simultaneously.
the ultrasound imaging technique is chosen in the group consisting of functional ultrasound imaging, electromechanical wave imaging, shear-wave imaging, three-dimensional ultrafast ultrasound imaging, and four-dimensional ultrafast ultrasound imaging.
at step b), at least one of the following properties is fulfilled:
step b) is carried out by using a computed tomography technique.
step b) is carried out by using a γ-scintigraphy technique.
step b) is carried out by using a positron emission tomography technique.
γ-rays are detected, the detection of γ-ray being in coincidence.
step a) being carried out at a first plurality of time instants, step b) is carried out at a second plurality of time instants and wherein at least one time instant of the first plurality being equal to one time instant of the second plurality.
the method further comprises the steps of d) evaluating the attenuation of a γ-ray by the presence of ultrasound waves, and e) compensating the evaluated attenuation by using a computed tomography technique.
step b) and step e) are carried out simultaneously.
the object is a biological object studied and the determined properties (P) enables to achieve an angiography of the object.

The present specification also describes a device for determining at least one property of an object, the device comprising:
a first imager adapted to image an object according to a first imaging modality, the first imaging modality being an ultrasound imaging technique imaging the object at a frame rate superior to 300 Hz,
a controller adapted to control the first imager to obtain first data relative to the object, and
a second imager adapted to image the object according to a second imaging modality based on the detection of rays, each detected ray being a X-ray or a γ-ray,
the controller being further adapted to control the second imager to obtain second data relative to the object and the controller being further adapted to determine the at least one property of the object based on the first data and the second data.

According to further aspects of the invention which are advantageous but not compulsory, the device which is described in the present specification might incorporate one or several of the following features, taken in any technically admissible combination:
the second imager is a computed tomography imager.
the second imager is a y-scintigraphy imager.
the second imager is a y-tomography imager.
the second imager is a positron emission-tomography imager.

The specification also describes a method for treating a disease of an area of a subject, the method comprising the steps of:
applying ultrasound waves in a continuous way on the area to be treated,
imaging the object according to a modality based on the detection of rays, each detected ray being a X-ray or a γ-ray, to obtain images, and
using the images to control the application of the ultrasound waves.

Such combination of X-ray/γ-ray with ultrasound waves enables to obtain better treatment of a disease since the application of ultrasound is controlled by the imaging step.

BRIEF DESCRIPTION OF THE DRAWINGS

The invention will be better understood on the basis of the following description which is given in correspondence with the annexed figures and as an illustrative example, without restricting the object of the invention. In the annexed figures.

DETAILED DESCRIPTION OF SOME EMBODIMENTS

Figure 1:
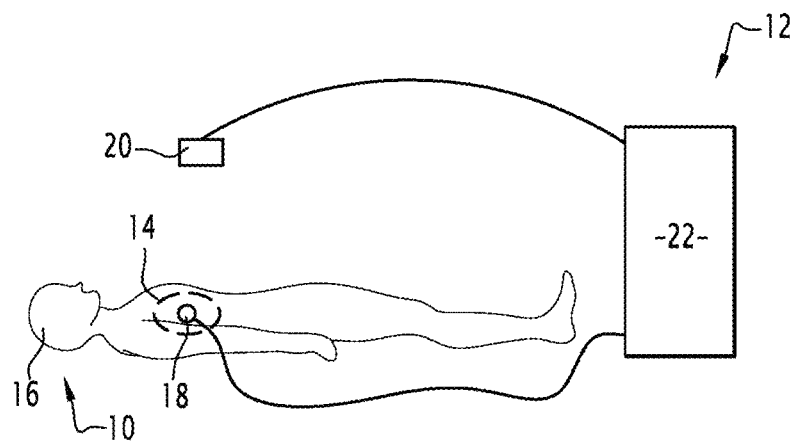
FIG. 1 shows schematically an object to be analyzed and a device for determining at least one property of the object.

An object 10 and a device 12 are represented on FIG. 1.

In the specific example of FIG. 1, the object 10 is an area 14 of a subject 16.

The area 14 is delimited on FIG. 1 by a dotted line.

The area 14 is, for instance, a portion of the lung.

The subject 16 of FIG. 1 is a human being.

Alternatively, the subject 16 is an animal.

The device 12 is device adapted to determine at least one property P of the object 10.

For instance, in the specific example of FIG. 1, the device 12 is adapted to determine if a tumorous cell is present in the area 14. In such case, the determined property P is the presence of a tumorous cell.

Figure 2:
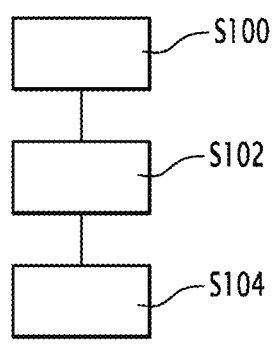
FIG. 2 shows schematically a flowchart illustrating an example of carrying out a method for determining at least one property of the object.

The device 12 is also adapted to carry out a method for determining at least one property P of the object 10 as described in reference to FIG. 2.

The device 12 comprises a first imager 18, a second imager 20 and a controller 22.

The first imager 18 is adapted to image the object 10 according to a first imaging modality.

The first imaging modality is an ultrasound imaging technique imaging the object 10 at a frame rate superior to 300 Hz.

The frame rate is the number of images per time unit that the first imager 18 is adapted to obtain.

This means that the first imager 18 is adapted to carry out an ultrafast ultrasound imaging technique.

According to a preferred embodiment, the first imager 18 is adapted to image the object 10 at a higher frame rate, for instance, the frame rate is superior to 500 Hz or superior to 800 Hz.

In the specific example, the first imager 18 comprises an ultrasound probe adapted to produce unfocused waves.

According to particular embodiment, the ultrasound probe is adapted to apply multiple ultrasound plane waves simultaneously. This also results in unfocused waves being applied to the object 10.

For instance, the ultrasound probe is adapted to apply at least 100 waves simultaneously to the object 10.

In the example, the ultrasound probe is an array of ultrasound transducers.

The number of ultrasound transducers is named n.

The number n is, for instance, comprised between 64 and 256.

To obtain a bi-dimensional image, the array of ultrasound transducers is a one-dimension bar.

The second imager 20 is adapted to image the object 10 with a second imaging modality.

The second imaging modality is based on the detection of rays, each detected ray being a X-ray or a γ-ray.

This means that with the second imaging modality, according to the cases, the detected rays are only X-rays, only γ-rays or a mixture of X-rays and γ-rays. For instance, the second imager 20 is a computed tomography imager. Such second imager 20 is also named a CT-imager.

In such case, the second imager 20 is adapted to image the object 10 by using X-rays.

The controller 22 is adapted to control the first imager 18 to obtain first data D1 relative to the object 10.

The controller 22 is further adapted to control the second imager 20 to obtain second data D2 relative to the object 10.

The controller 22 is also adapted to determine the property P of the object 10 based on the first data D1 and the second data D2.

For instance, according to a specific embodiment; the controller 22 comprises an electronic circuitry, a processor and a set of (n+1) memories.

The electronic circuitry is adapted to command both the first imager 18 and the second imager 20.

Notably, the electronic circuitry is adapted to make the array of ultrasound transducers emit ultrasound waves and receive the ultrasound waves reflected by the area 14 of the subject 16.

The electronic circuitry is adapted to command the second imager 20 to collect the X-rays present in the area 14 of the subject 16.

As a specific illustration, the electronic circuitry comprises n+1 analogue-to-digital converters and the n+1 memories.

n analogue-to-digital converters are connected to a respective ultrasound transducer of the ultrasound probe of the first imager 18 while one analogue-to-digital converter is connected to the second imager 20.

Similarly, each memory is connected to a respective analogue-to-digital converter.

The processor is adapted to communicate with the memories.

The processor is further adapted to process the ultrasound signals received by the ultrasound probe of the first imager 18 to obtain the first data D1.

Similarly, the processor is further adapted to process the X-ray signals collected by the imager 20 to obtain the second data D2.

The processor uses both first data D1 and second data D2 to determine a property P of the object 10.

Operation of the device 12 is now described in reference to the flowchart of FIG. 2 which illustrates an example of carrying out a method for determining at least one property P of the object 10.

As an example, the determined property P is the presence of a tumorous cell and the object 10 is the area 14.

According to the example of FIG. 2, the method for determining comprises three steps which are a step S100 of obtaining first data D1, a step S102 of obtaining second data D2 and a step S104 of determining the property P of the object 10.

At the step S100 of obtaining first data D1, the first imager 18 images the object 10 according to the first modality.

This means that ultrasound waves are used and that the frame rate is superior to 300 Hz.

The ultrasound waves are applied to the area 14.

For this, the ultrasound probe of the first imager 18 is used.

The obtained first data D1 are relative to the area 14.

For instance, the obtained first data D1 are images.

At the step S102 of obtaining second data D2, the second imager 20 images the area 14 by using X-rays.

More precisely, a CT imaging technique is used at the step S102.

The obtained first data D2 are relative to the area 14.

For instance, the obtained first data D2 are images.

At the step S104 of determining, the presence of a tumorous cell is detected based on the first data D1 and the second data D2.

More precisely, by using images obtained by ultrasound and by X-ray, the controller 22 is able to determine the presence of a tumorous cell in the area 14.

In such method, the determination of the presence of tumorous cell(s) is combining data obtained by ultrafast ultrasound imaging with data obtained by a technique involving X-ray.

Such method enables to obtain a property P (in this case the detection of tumorous cell(s)) which allows achieving molecular imaging at UUI spatial and temporal resolution.

According to an embodiment, step a) is carried out at a first plurality of time instants, step b) is carried out at a second plurality of time instants and wherein at least one time instant of the first plurality being equal to one time instant of the second plurality.

This ensures that at least one data of the first data D1 and one data of the second data D2 are taken simultaneously.

This facilitates exploiting the data since at least some of the first data D1 and the second data D2 corresponds to the same physical image.

Such effect is strengthened when each time instant of the first plurality is a time instant of the second plurality and vice-versa.

According to an embodiment, the applied ultrasound waves at step S100 are unfocused waves.

An unfocused ultrasound wave is a wave for which an aperture is defined.

The aperture has a specific size labeled D.

An ultrasound wave is considered as unfocused if the minimal width $W_{min}$ of the ultrasound beam associated to the ultrasound wave at a depth F is larger than the ratio of the product of the wavelength λ of the ultrasound wave by the depth F with the specific size D of the aperture. Such condition may be mathematically expressed as:

$$W_{min} > \frac{\lambda * F}{D}$$

This means that the unfocused waves are plane waves or divergent waves or multiple focus waves (corresponding to several simultaneous focused beams at different locations transmitted by aperture D).

In another embodiment, step S100 for obtaining the first data D1 further comprises the sub-steps of emitting the ultrasound waves towards the object 10, collecting the ultrasound waves reflected by the object 10, using the collected ultrasound waves to obtain images and analyzing the images to obtain the first data D1.

In such embodiment, the step S100 is an ultrasound imaging substep according to the first imaging modality combined with an analyzing substep.

According to a specific example, the image area obtained at the imaging substep is superior or equal to 1.0 cm².

Any ultrafast ultrasound technique may be used for the first imaging modality.

The first imaging modality may be functional ultrasound imaging.

According to another embodiment, the first imaging modality may be electromechanical wave imaging.

Alternatively, the first imaging modality is shear-wave imaging.

In another embodiment, the first imaging modality is a three-dimensional ultrafast ultrasound imaging.

For instance, the used method is 3D Ultrafast Ultrasound Imaging (see Provost et al., 2014b) that can image at thousands of volumes per second based on the use of a customized 1024-channel ultrasound scanner (commercial scanners typically do not exceed 256 channels) and a 2-D array probe. By emitting 3-D dimensional diverging waves such as plane and spherical waves, such method enable to image that motion and blood flow in entire 3D fields of views by achieving imaging rates that are superior to 300 Hz.

According to another embodiment, the first imaging modality is a four-dimensional ultrafast ultrasound imaging, the four dimension being the time.

Any ultrafast ultrasound technique combining the previous mentioned techniques may be considered for the first imaging modality.

According to a specific embodiment, the step S102 is carried out by combining a X-ray technique and a γ-ray technique.

For instance, the method further comprises the steps of evaluating the attenuation of a γ-ray by the presence of ultrasound waves and compensating the evaluated attenuation by using a computed tomography technique.

Advantageously, the step S102 and the step of compensating are carried out simultaneously.

According to another embodiment, the step S102 is carried out by using a γ-scintigraphy technique.

According to such embodiment, the imager 20 is a γ-scintigraphy imager.

According to another embodiment, the step S102 is carried out by using a single-photon computed tomography (SPECT) technique.

According to still another embodiment, the step S102 is carried out by detecting γ-rays in coincidence.

In such context, the second imaging modality is, for instance, γ-tomography.

According to another embodiment, the step S102 is carried out by using a positron emission tomography (PET) technique.

In such embodiment, a novel imaging modality that combines Positron Emission Tomography with Ultrafast Ultrasound Imaging is obtained. Positron emission tomography is the most sensitive molecular imaging modality and as such can be used characterize subtle biological pathways in vivo but cannot image tissue structure and suffers from poor spatial and temporal resolution. Ultrafast Ultrasound Imaging, on the other hand, can be performed at thousands of image per second with a 100-micron resolution to quantitatively map the function and structure of tissues. The development of such method will allow for the synergistic combination of PET and UUI to achieve molecular imaging at UUI spatial and temporal resolution through the advancement of wave and fundamental physics. As a result, such method will have the unique capability of simultaneously imaging the biochemistry, function, and structure, which will be leveraged to define novel pre-clinical research avenues and clinical diagnostic protocols.

Such method has therefore several field of application.

The object 10 may be a living tissue in-vivo or ex-vivo.

According to a specific, the object 10 is an artificial heart.

Notably, when the object 10 is a biological object studied in a field, the field being oncology, cardiology or neurology, application of such method may be considered in oncology, cardiology or neurology.

In oncology, such a method would allow for the simultaneous imaging of the 2-deoxy-2-[$^{18}$F]fluoro-D-glucose (FDG) uptake using PET and of the microvasculature using Ultrafast Doppler techniques. FDG imaging using PET is the reference technique to stage cancer and assess therapeutic efficacy. On the one hand, it has been shown that cell proliferation requires a vascular network and the creation of new vessels via angiogenesis. Preventing tumors from recruiting their own vascular network using anti-angiogenesis drugs should therefore inhibit their growth. However, while anti-angiogenesis drugs are very active in late stage metastasis in specific sites, they aren't in earlier stages and in other sites. A better understanding of these processes is thus necessary and recent studies indicate that characterizing the relationship between the vascular network and the energy metabolism of tumors might be useful in identifying responders.

In cardiology, a major source of death and disability is the interruption of blood flow to the heart, which create an ischemia and eventually a loss in myocardial function. Inversely, metabolic diseases such as diabetes increase the risk of such complications two to three-fold. The correlation of PET imaging to quantify the viability of cardiac tissue with the capability of cardiac Shear-Wave Imaging in UUI to quantify the active (systolic) and passive (diastolic) properties could lead, e.g., to the development of fully non-invasive novel ultrasound biomarkers to assess for the viability of cardiac tissues and lead to a better understanding of the relationship between cardiac function, vascularization, and metabolism.

In neurology, PET imaging of inflammation using radiotracers such as FDG along with functional ultrasound imaging of the brain vasculature and activation could provide new research avenues in brain disease models. Brain activation maps obtained using functional ultrasound could also be correlated with molecular activity to enhance our understanding of the hemodynamic response and the brain physiology.

This example only illustrates the possible application of such method, bearing in mind that many other possibilities may be considered.

In accordance, the property of the object 10 to be determined may be any property.

In a specific example, the property is the limits of an area to be treated.

According to another example, the property is the presence of tumorous cells.

This also means that the first data D1 and the second data D2 may be of various kinds.

In most embodiments, the first data D1 are anatomical and/or physiological data while the second data D2 are functional and/or molecular data.

However, other embodiments may be considered.

For instance, in a specific embodiment, the first data D1 are the movement of the object and wherein the step S104 of determining the property comprises correcting the images obtained at step S102 based on the first data D1, to obtain reconstructed images.

Such method also opens the way to more efficient therapy, notably when a method for treating a disease of the area 14 is considered.

As an example, such method comprises the steps of applying ultrasound waves in a continuous manner on the area to be treated, imaging the object with at least one of a X-ray and a γ-ray, to obtain images and using the images to control the application of the ultrasound waves.

In such case, by continuous, it is to be understood that ultrasound waves are applied during a time duration superior to one second.

Several aspects should also be emphasized at this point.

According to a first aspect, step a) is carried out with an ultrasound probe which is hold by a support.

By the term "support" in this context, it is meant a device which maintains the ultrasound probe in a stable position.

In an embodiment, the support is displaceable, notably in a controlled way.

According to an example, the support is a rod linked to a micropositioner. The rode is, for instance, made in carbon.

In a specific embodiment, the position of the ultrasound probe is controlled by using a six-degree-of-freedom, motorized, positioning system.

This means that step a) is carried out with an ultrasound probe which is not held by an operator.

By contrast, in document US 2015/0305700 A1, it is an operator which holds the ultrasound probe.

This induces a strong dependency with the know-how of the operator.

According to a second aspect, step a) comprises displacing the ultrasound probe in function of the movement of the object 10 from one image to another image.

This means that the support of the ultrasound probe is displaced in the basis on the displacement of the area of interest in the image.

In variant or in complement, step a) comprises displacing the ultrasound probe in function of hemodynamics data.

Such second aspect is not possible with an ultrasound probe hold by an operator.

According to a third aspect, the determined property is a cartography of small vessels. This enables to realize Doppler angiography.

In such case, the high quality of the morphologic imaging is advantageously used.

Other aspects will be further detailed in the following section.

EXPERIMENTAL SECTIONS

Several studies using the device 12 and made by the Applicant are detailed. As a precaution, in case those studies were published before the date of filing of the current patent application, the grace period, if applicable, is requested.

First Study

Introduction

In this study, it is introduced a novel device capable of simultaneously performing Positron Emission Tomography (PET) and Ultrafast Ultrasound Imaging (UUI). PET is a sensitive molecular imaging modality and can be used to characterize subtle biological pathways in vivo but cannot image tissue structure. UUI, on the other hand, can be performed at thousands of image per second with a 100-micron resolution to quantitatively map functions such as blood flow and the structure of tissues. The objective of this study was to demonstrate the feasibility of simultaneous PET/UUI imaging in small animals for pre-clinical studies.

Methods

The PET/UUI device was built by combining an Aixplorer system (Supersonic Imagine, France) with a PET/CT Nano-PET scanner (Mediso, Hungary). Marker-less, rigid-body co-registration was achieved between the two modalities by controlling the position of the ultrasound probe using a six-degree-of-freedom, motorized, positioning system (Hexapod H811, Physik Instrumente, Germany). A 15-MHz ultrasound probe (Vermon, France) was used to map blood vessels at a resolution of approximately 100 μm in the Ultrafast Doppler Imaging mode within a 2×1.5×1.3-cm$^3$ volume. PET was acquired during 60 min after [18F]-fluorodeoxyglucose (FDG) IV injection. The quality of the co-registration and the effect of presence of the ultrasound probe were assessed in phantoms and the PET/UUI sequence was applied in vivo in tumors implanted subcutaneously in nude mice.

Results

The phantom study demonstrated that both Ultrafast Doppler Imaging and PET imaging could be performed simultaneously with sub-resolution co-registration accuracy (0.95±0.28 mm; n=10) and limited effect of the presence of an ultrasound probe inside the PET tube on the PET image quality. The in vivo study demonstrated the feasibility of simultaneously displaying the CT scan of the bone structure of the mouse; the PET image of FDG accumulation in the tumor; and the Ultrafast Power Doppler image of the vasculature in the tumor.

Conclusions

These initial results demonstrate the feasibility of simultaneous PET and Ultrafast Doppler Imaging for the study of the relationship between angiogenesis and metabolism in tumors and more generally the viability of a PET/UUI approach.

Second Study

Background, Motivation and Objective

The development of novel diagnostic tools and treatments for our most pressing healthcare challenges such as cancer can tremendously benefit from a complete understanding of the multifactorial, multi-scale biological underpinnings involved. In this study, it is introduced a novel device capable of simultaneously performing Positron Emission Tomography (PET) and Ultrafast Ultrasound Imaging (UUI). PET is the most sensitive molecular imaging modality and as such can be used to characterize subtle biological pathways in vivo but cannot image tissue structure and suffers from poor spatial and temporal resolution. UUI, on the other hand, can be performed at thousands of images per second with a 100-micron resolution to quantitatively map function (such as blood flow) and the structure of tissues. The objective of this study was to demonstrate the feasibility of simultaneous PET/UUI imaging in small animals for pre-clinical studies.

Statement of Contribution/Methods

The PET/UUI device was built by combining an Aixplorer system (Supersonic Imagine, France) with a PET/CT Nano-PET scanner (Mediso, Hungary). A 15-MHz ultrasound probe (Vermon, France) was motorized within the PET tube using a single-axis linear stage (Physik Instrumente, Germany). Ultrafast Doppler Imaging was performed using repeated 2D 400-ms-long, 500-fps compounded tilted plane wave acquisitions (−10 to 10 degrees with a 2 degree increment) over an elevational scanning range of 1 cm with a 200-um step size. The PET acquisition lasted 15 minutes. A CT scan was performed prior to the PET/UUI acquisitions for spatial co-registration and PET attenuation correction. A bi-modality flow phantom consisting of a twisted tygon tube filled with a blood phantom mixed with a controlled concentration of fludeoxyglucose-F-18 (FDG) put in motion using a syringe pump was used to assess the effect on the quantification capabilities of PET in the presence of an ultrasound probe near the photodetectors. The PET/UUI Power Doppler sequence was then applied in vivo in a subcutaneous allografted tumor model in a nude mouse after the intravenous administration of 10 MBq.

Results/Discussion

The phantom study demonstrated that Ultrafast Doppler Imaging and PET imaging could be performed simultaneously. While the ultrasound probe did modify the PET image, its effects were deemed insignificant after CT-based attenuation correction. The in vivo study demonstrated the feasibility of simultaneously displaying the CT scan of the bone structure of the mouse; the PET image of the FDG accumulation in the tumor; and the Ultrafast Power Doppler image of the vasculature surrounding the tumor. These initial results demonstrate the feasibility of simultaneous PET and Ultrafast Doppler Imaging for the study of the relationship between angiogenesis and metabolism in tumors and more generally the viability of a PET/UUI approach.

Third Study

Introduction

Hybrid systems for biomedical imaging synergistically enhance the information extracted from a single modality such as coupling of PET with MRI for combined molecular and anatomical/functional imaging. Recent developments in Ultrafast Ultrasound Imaging (UUI) has allowed for the imaging of the microvasculature in vivo. The Applicant recently built PETRUS, a hybrid system combining PET with UUI that enables the visualization and direct correlation of metabolic information from PET with high resolution anatomical and functional images from UUI. In this work, the Applicant has quantified: the accuracy of marker-less PET/UUI registration and (the influence of the ultrasound (US) probe on the PET images.

Methods:

PETRUS is based on a small animal PET/CT system (Nanoscan PET/CT, Mediso) in which a six-degree-of-freedom motorized micropositioner (Hexapod H811, Physik Instrumente, Germany) moves an ultrasound probe connected to an Aixplorer UUI system (Supersonic Imagine, France). For the initial co-registration, the CT module of the PET-CT system was used as an intermediate modality. A phantom consisting of three 140-μm gutta percha tips (Atopointes, A.T.O Zizine, France) was positioned inside a water bath. The initial CT/UUI affine transformation was then retrieved from the CT and UUI images of the tips. The positions of UUI images for the subsequent movements of the Hexapod are calculated by taking into account the changes of the axis values of the latter. In a second series of measurements, the PET signal was measured in a NEMA phantom filled with 2-deoxy-2-[18F]fluoro-D-glucose (FDG) with and without the presence of the US probe.

Results:

A registration the US and the CT images of the tips wad achieved. The error of the registration was 0.13±0.02 mm (n=5). For the US probe attenuation experiment, the US probe reduced the FDG signal (Bq/ml) by 7.5±1.5% directly under the US probe, but remained unaffected elsewhere.

Conclusions:

PETRUS is a novel hybrid imaging modality capable of acquiring PET and UUI images simultaneously with a registration accuracy below the resolution limit of PET. While the presence of the US probe had an effect on the PET signal, it can be accounted and corrected for in order to register the FDG uptake with anatomical and functional imaging of the vascular system.

Fourth Study

Altered energetic metabolism and abnormal vasculature are two hallmarks of cancer tightly related to each other. Here the Applicant used a reverse genetics approach to explore the effects of mutations in key steps of the glucose metabolism pathway on tumor vessel network and in response to the receptor tyrosine kinase inhibitor sunitinib, using FDG-PET with DCE-MRI and Ultrasensitive Doppler.

Mutations introduced in CCL39 Ras-transformed fibroblasts (WT) were: (1) Gly−, phosphohexoisomerase deficient, non glycolytic; (2) Res−, respiration deficient; (3) MCT4+, monocarboxylate transporter type 4 for lactate export. Cell lines were implanted in the flanks of nude mice. DCE-MRI (4.7 T MR; Bruker) and FDG-PET (nanoScan PET-CT; Mediso) were performed before and after administration of sunitinib. Tissue blood flow (BF) and volume fraction (BV) were calculated using in-house software (PhysioD 3D). In additional mice, remote-controlled Ultrasensitive Doppler of the tumors was acquired during the PET acquisition using our newly developed PETRUS system combining the nanoScan PET-CT with an Aixplorer scanner (Supersonic Imagine).

Compared to WT, tumor uptake of FDG was reduced in Gly− and increased in Res− and MCT4+. Assessment of perfusion parameters suggested that tumor types can be grouped into three vascular profiles: highly (Gly−), moderately (WT) and poorly vascularized (MCT4+ and Res−). Simultaneous images of the tumor vascular network and hypermetabolic areas automatically registered at the submillimeter level confirmed these results. Based on FDG uptake and vascular parameters, tumor response to sunitinib was highly dependent on their metabolism profile. BF and BV were increased after sunitinib in MCT4+ (BF: 3±1 vs 14±5 ml/min/100 ml) and Res− (BF: 7±3 vs 11±4 ml/min/100 ml), and decreased in WT (BF: 32±11 vs 17±6 ml/min/100 ml). Changes in Gly− tumours were not significant. A decrease in FDG SUVmax was observed in MCT4+(4.4±1.1 vs 3.4±1.0) and Res− (SUVmax: 4.9±1.2 vs 3.4±1.1), while it increased in WT (3.3±0.8 vs 4.1±0.9), and remained constant in Gly− tumors (1.6±0.5 vs 1.5±0.3).

Vascular parameters depend on the energetic metabolic tumor phenotype. A short course of sunitinib rapidly increased capillarity and decreased FDG uptake in tumors of poor prognosis, such as an exclusive anaerobic glycolytic metabolism, or MCT4 transporter expression. In exclusively aerobic metabolism, vascular parameters and FDG uptake were not significantly modified by sunitinib.

Fifth Study

Anti-angiogenic chemotherapy aims to prevent tumor development by blocking the formation of neo vessels, but may also induce severe systemic side effects such as impaired heart function and hypertension. During a PET imaging study with the multi-targeted receptor tyrosine kinase inhibitor sunitinib, we serendipitously observed an increase in 2-deoxy-2[18F]fluoro-D-glucose (18FDG) uptake in the myocardium of nude mice. Here, we explored further with PET the effect of sunitinib on the myocardium.

Four groups of mice (aged 17-20 w) were compared: (1) nude mice treated with sunitinib 50 mg·kg-1 (n=9), (2) nude mice treated with placebo (DMSO+PBS) (n=6), (3) C57Bl6 mice treated with sunitinib 50 mg·kg-1 (n=6), (4) C57Bl6 mice treated with placebo (n=6).

Mice were fasted and a baseline PET dataset was acquired in a nanoScan PET-CT camera (Mediso, Hungary) during 60 min after IV injection of 10 MBq $^{18}$FDG. Mice were then treated by gavage with sunitinib or placebo during 5 days, followed by a post-treatment PET-CT at day 7. Heart FDG images were analyzed using PMOD software. C57Bl6 mice were also explored by echocardiography at baseline and post-treatment using a Vevo 2100 (VisualSonics, Canada).

Compared to baseline, SUV was increased by 50±13 percent in nude mice treated with sunitinib (p=0.0003) while it increased only by 17±26 percent in the placebo-treated group (n.s). In the sunitinib group, compartmental modeling demonstrated an increase of 57±11 percent of the glucose influx in the myocardium associated with a decrease of glucose uptake compared to baseline (p=0.002; p=0.001), while these parameters remained unchanged in the placebo group. However, lectine immunostaining reveals showed no difference in the number of capillaries between groups.

In C57Bl6 mice, PET results were similar and moreover, sunitinib-treatment induced a dramatic reduction of cardiac output down by 59±36 percent (p=0.01), while in placebo-treated mice there was a slight increase of 13±22 percent (n.s).

In conclusion, FDG PET-CT imaging shows that glucose uptake is dramatically increased by sunitinib treatment. These data suggest that sunitinib treatment is associated with a metabolic dysregulation that could be the consequence of vascular function impairment. Work is in progress in our laboratory to better clarify mechanism of chemotherapy-induced cardiotoxicity, particularly the link between vascular function and metabolism using PETRUS-PET Pet Registered Ultrafast Sonography.

The embodiments and alternative embodiments considered here-above in the sections "detailed description of some embodiments' and "experimental section" can be combined to generate further embodiments of the invention.

The invention claimed is:

1. A method for determining at least one property of an object, the method comprising steps of:
   a) obtaining first data relative to the object by imaging the object according to a first imaging modality, the first imaging modality being an ultrasound imaging technique imaging the object at a frame rate superior to 300 Hz with ultrasound waves, wherein the first imaging modality is carried out with an ultrasound probe which is maintained in a stable position using a support and without an operator holding the ultrasound probe or support, and wherein at least one of the following properties is fulfilled for the first imaging modality:
   the first imaging modality comprises applying unfocused ultrasound waves,
   the first imaging modality comprises applying multiple ultrasound plane waves simultaneously,
   the ultrasound imaging technique is chosen from a group consisting of functional ultrasound imaging, electromechanical wave imaging, shear-wave imaging, three-dimensional ultrafast ultrasound imaging, and four-dimensional ultrafast ultrasound imaging,
   b) obtaining second data relative to the object by imaging the object according to a second imaging modality based on detection of rays, each detected ray being an X-ray or a γ-ray,
   c) determining the at least one property of the object based on the first data and the second data,
   d) evaluating an attenuation of at least one of the detected γ-rays by the ultrasound waves, and
   e) compensating the evaluated attenuation by using a computed tomography technique,
   wherein images are obtained at step b), the first data being a movement of the object, and wherein step c) comprises correcting the images obtained at step b) based on the first data, to obtain reconstructed images.

2. The method according to claim 1, wherein the support is displaceable.

3. The method according to claim 1, wherein the support is a rod maintained by a positioner.

4. The method according to claim 1, wherein step a) comprises displacing the ultrasound probe in function of a movement of the object from one image to another image.

5. The method according to claim 1, wherein step a) further comprises displacing the ultrasound probe in function of hemodynamics data.

6. The method according to claim 1, wherein at step b), at least one of the following properties is fulfilled:
- step b) is carried out by using a computed tomography technique;
- step b) is carried out by using a γ-scintigraphy technique;
- step b) is carried out by using a positron emission tomography technique;
- γ-rays are detected, the detection of γ-ray being in coincidence; and
- step a) being carried out at a first plurality of time instants, step b) is carried out at a second plurality of time instants, and wherein at least one time instant of the first plurality being equal to one time instant of the second plurality.

7. The method according to claim 1, wherein step b) and step e) are carried out simultaneously.

8. The method according to claim 1, wherein the object is a biological object studied and the determined properties enables achieving an angiography of the object.

9. A device for determining at least one property of an object, the device comprising:
- a first imager adapted to image an object according to a first imaging modality, the first imaging modality being an ultrasound imaging technique imaging the object at a frame rate superior to 300 Hz with ultrasound waves, the first imager comprising an ultrasound probe configured to carry out the first imaging modality and a support configured to maintain the ultrasound probe in a stable position without an operator holding the ultrasound probe or support, wherein at least one of the following properties is fulfilled for the first imaging modality:
  - the first imaging modality comprises applying unfocused ultrasound waves,
  - the first imaging modality comprises applying multiple ultrasound plane waves simultaneously, and
  - the ultrasound imaging technique is chosen from a group consisting of functional ultrasound imaging, electromechanical wave imaging, shear-wave imaging, three-dimensional ultrafast ultrasound imaging, and four-dimensional ultrafast ultrasound imaging,
- a controller adapted to control the first imager to obtain first data relative to the object, wherein the first data is a movement of the object based on images obtained with the first imager, and
- a second imager adapted to image the object according to a second imaging modality based on the detection of rays, each detected ray being an X-ray or a γ-ray, the controller being further adapted to control the second imager to obtain second data relative to the object, the controller being further adapted to determine the at least one property of the object based on the first data and the second data, wherein the controller is adapted to correct images obtained with the second imager based on the first data to obtain reconstructed images, the device being further adapted to evaluate an attenuation of at least one of the detected γ-rays by the ultrasound waves, and compensate the evaluated attenuation by using a computed tomography technique.

10. The device according to claim 9, wherein the second imager is a computed tomography imager or a γ-scintigraphy imager.

11. A method for treating a disease of an area of a subject, the method comprising the steps of:
- applying ultrasound waves in a continuous way on the area to be treated, the step of applying being carried out with an ultrasound probe which is maintained in a stable position using a support and without the operator holding the ultrasound probe or support,
- imaging the area of the subject according to a modality based on detection of rays, each detected ray being an X-ray or a γ-ray, to obtain images,
- correcting the images obtained during the imaging step based on data related to a movement over the area to be treated in the applying step to obtain reconstructed images,
- using the images to control the application of the ultrasound waves,
- evaluating an attenuation of at least one of the detected γ-rays by the ultrasound waves, and
- compensating the evaluated attenuation by using a computed tomography technique.

* * * * *